United States Patent
Loughner et al.

(10) Patent No.: US 8,999,891 B2
(45) Date of Patent: Apr. 7, 2015

(54) METHOD FOR CONTROLLING WEEDS IN TURF

(71) Applicant: Dow AgroSciences LLC, Indianapolis, IN (US)

(72) Inventors: Daniel Louis Loughner, Lawrenceville, NJ (US); Andrea Christine McVeigh-Nelson, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/198,379

(22) Filed: Mar. 5, 2014

(65) Prior Publication Data

US 2014/0256552 A1  Sep. 11, 2014

Related U.S. Application Data

(60) Provisional application No. 61/773,343, filed on Mar. 6, 2013.

(51) Int. Cl.
*A01N 43/40* (2006.01)
*A01N 43/90* (2006.01)

(52) U.S. Cl.
CPC ............... *A01N 43/90* (2013.01); *A01N 43/40* (2013.01)

(58) Field of Classification Search
None
See application file for complete search history.

(56) References Cited

U.S. PATENT DOCUMENTS

2009/0215797 A1   8/2009   Hopkins et al.
2010/0267559 A1   10/2010  Loughner et al.

FOREIGN PATENT DOCUMENTS

WO   2012/049266 A1   4/2012

OTHER PUBLICATIONS

Lickfeldt et al., "Three-Way Fluroxypyr Herbicides for Postemergent Broadleaf Weed Control in Turf," Nov. 14, 2006. [Retrieved on May 15, 2014]. Retrieved from the Internet. <URL:https://crops.confex.com/crops/2006am/techprogram/P22655.HTM>.

*Primary Examiner* — Alton Pryor
(74) *Attorney, Agent, or Firm* — Michael J. Terapane; Meunier Carlin & Curfman, LLC.

(57) ABSTRACT

Undesirable vegetation is controlled in turf using a combination of (a) florasulam, (b) 2,4-D or an agriculturally acceptable salt or ester thereof, and (c) fluoroxypyr or an agriculturally acceptable salt or ester thereof.

15 Claims, No Drawings

METHOD FOR CONTROLLING WEEDS IN TURF

CROSS REFERENCE TO RELATED APPLICATIONS

This application claims the benefit of U.S. Provisional Patent Application Ser. No. 61/773,343 filed Mar. 6, 2013, the disclosure of which is expressly incorporated herein by reference.

BACKGROUND

Annual market research reports consistently identify white clover (*Trifolium repens*) and dandelion (*Taraxacum officinale*) as the two key broadleaf weed targets for weed control in turf. In addition, ground ivy (*Glechoma hederacea*) and wild violet (*Viola* sp.) are identified as difficult to control weeds. There remains a need for methods that are effective in controlling these weeds in turf.

US20090215797 describes herbicidal formulations comprising 3.3 grams per liter (g/L) florasulam, 320 g/L 2,4-D, and 46.8 g/L fluoroxypyr-meptyl.

SUMMARY

Provided herein is a method for controlling undesirable vegetation in turf which comprises applying a synergistic combination of (a) florasulam (b) 2,4-D or an agriculturally acceptable salt or ester thereof, and (c) fluoroxypyr or an agriculturally acceptable salt or ester thereof.

DETAILED DESCRIPTION

Definitions

Fluoroxypyr is the common name for [(4-amino-3,5-dichloro-6-fluoro-2-pyridinyl)oxy]acetic acid. As described in Tomlin, C. D. S., Ed. *The Pesticide Manual: A World Compendium*, 15$^{th}$ ed.; BCPC: Alton, 2009 (hereafter "The Pesticide Manual"), fluoroxypyr is effective by post-emergence foliar application, controlling a large range of economically important broad-leaved weeds, including, e.g., *Rumex* spp. and *Uritica dioica* in pastures and *Trifolium repens* in amenity grassland. The molecular weight of fluoroxypyr is 255.0. Exemplary chemical forms of fluoroxypyr include salt or ester forms. Fluoroxypyr-meptyl is 1-methylheptyl [(4-amino-3,5-dichloro-6-fluoro-2-pyridinyl)oxy]acetate. The molecular weight of fluoroxypyr-meptyl is 367.2. It is a solid and is typically formulated as an emulsifiable concentrate at a concentration of about 26 weight percent in aromatic hydrocarbon solvents (for example, Dow AgroSciences' Starane™ herbicide). Aromatic hydrocarbon solvents have historically been used to maintain stability at low temperature in fluoroxypyr-meptyl formulations.

Florasulam is the common name for 2',6',8-trifluoro-5-methoxy[1,2,4]triazolo[1,5-c]pyrimidine-2-sulfonanilide. As described in *The Pesticide Manual*, florasulam is used for post-emergence control of broad-leaved weeds in cereals and maize at rates of up to 7.5 grams active ingredient per hectare (g ai/ha).

2,4-D is the common name for (2,4-dichlorophenoxy)acetic acid. Exemplary uses of 2,4-D described in *The Pesticide Manual* include its use for post-emergence control of annual and perennial broadleaf weeds, e.g., in cereals, maize, sorghum, grassland, established turf, grass seed crops, orchards, cranberries, asparagus, sugarcane, rice forestry and non-crop land. Exemplary chemical forms of 2,4-D include salt or ester forms, for example, 2,4-D EHE, which is 2-ethylhexyl(2,4-dichlorophenoxy)acetate; 2,4-D DMA, which is N-methylmethanaminium (2,4-dichlorophenoxy)acetate; and 2,4-D choline, which is 2-hydroxy-N,N,N-trimethylethanaminium (2,4-dichlorophenoxy)acetate.

As used herein, control of or controlling undesirable vegetation means killing or preventing the vegetation, or causing some other adversely modifying effect to the vegetation e.g., deviations from natural growth or development, regulation, desiccation, retardation, and the like.

As used herein, herbicide and herbicidal active ingredient mean a compound that controls undesirable vegetation when applied in an appropriate amount.

As used herein, a herbicidally effective or vegetation controlling amount is an amount of herbicidal active ingredient the application of which controls the relevant undesirable vegetation.

As used herein, applying an herbicide or herbicidal composition means delivering it directly to the targeted vegetation or to the locus thereof or to the area where control of undesired vegetation is desired. Methods of application include, but are not limited to pre-emergence, post-emergence, and foliar applications. Described herein are methods of controlling undesirable vegetation by applying certain herbicide combinations or compositions.

As used herein, plants and vegetation include, but are not limited to, dormant seeds, germinant seeds, emerging seedlings, plants emerging from vegetative propagules, immature vegetation, and established vegetation.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can by hydrolyzed, oxidized, metabolized, or otherwise converted, e.g., in plants, water, or soil, to the corresponding carboxylic acid which, depending upon the pH, may be in the dissociated or undissociated form.

Exemplary salts include those derived from alkali or alkaline earth metals and those derived from ammonia and amines. Exemplary cations include sodium, potassium, magnesium, and ammonium cations of the formula:

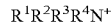

$$R^1R^2R^3R^4N^+$$

wherein $R^1$, $R^2$, $R^3$ and $R^4$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

As used herein, weight ratios of mixtures are calculated using the acid equivalent weight(s) of any compounds in the mixture that are salts or esters.

Methods

Provided herein is a method for controlling undesirable vegetation in turf which comprises applying a herbicidally effective amount of a combination of (a) florasulam, (b) 2,4-D or an agriculturally acceptable salt or ester thereof, and (c) fluoroxypyr or an agriculturally acceptable salt or ester thereof.

In certain embodiments the weight ratio of active ingredients applied is in the range of about 0.001 to 10.3 of (a) to about 0.11 to 1038 of (b) to about 0.01 to 105.4 of (c). In some embodiments the weight ratio of (a) to (b) is from about 1:50 to about 1:200, and the weight ratio of (a) to (c) is from about 1:5 to about 1:20. In some embodiments the weight ratio of (a) to (b) is from about 1:80 to about 1:140, and the weight ratio of (a) to (c) is from about 1:7 to about 1:13. In certain embodiments the weight ratio of (a) to (b) to (c) is about 1:110:10.

In certain embodiments the only herbicidal active ingredients applied are (a) florasulam, (b) 2,4-D or an agriculturally acceptable salt or ester thereof, and (c) fluoroxypyr or an agriculturally acceptable salt or ester thereof. In other embodiments additional herbicidal active ingredients may be applied.

The active ingredients may be applied together in a formulation which also contains an agriculturally acceptable adjuvant or carrier.

The combination of active ingredients utilized in the method exhibit synergism, e.g., the herbicidal active ingredients are more effective in combination than when applied individually. The *Herbicide Handbook* of the Weed Science Society of America, Ninth Edition, 2007, p. 429 notes that synergism is "an interaction of two or more factors such that the effect when combined is greater than the predicted effect based on the response of each factor applied separately." In certain embodiments, the compositions exhibit synergy as determined by the Colby's equation. Colby, S. R. Calculation of the synergistic and antagonistic response of herbicide combinations. *Weeds* 1967, 15, 20-22.

Herbicidal activity (control of undesirable vegetation) is exhibited by the compositions when they are applied directly to the plant or to the locus of the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. In some embodiments, the compositions described herein are applied to relatively immature undesirable vegetation to achieve the maximum control of weeds.

In some embodiments, the compositions and methods provided herein are utilized to control undesirable vegetation consisting of broadleaf weeds.

In some embodiments, the compositions and methods provided herein are utilized to control undesirable vegetation such as ground ivy (GLEHE), white clover (TRFRE), dandelion (TAROF) and prostrate spurge (EPHSU) in turf.

The application rate will depend upon the particular type of weed to be controlled, the degree of control required, and the timing and method of application. In some embodiments, the composition is applied at an application rate of from about 0.1 grams active ingredient per hectare (g ai/ha) to about 1200 g ai/ha based on the total amount of active ingredients in the composition.

In some embodiments the florasulam is applied at a rate from about 0.001 g ai/ha to about 10.3 g ai/ha, 2,4-D or an agriculturally acceptable salt or ester thereof is applied at a rate of from about 0.11 to about 1038 grams acid equivalent per hectare (g ae/ha), and fluoroxypyr or an agriculturally acceptable salt or ester thereof is applied at a rate of from about 0.01 to about 105.4 g ae/ha.

In some embodiments the florasulam is applied at a rate from about 0.001 g ai/ha to about 5.2 g ai/ha, 2,4-D or an agriculturally acceptable salt or ester thereof is applied at a rate of from about 0.11 to about 520 g ae/ha, and fluoroxypyr or an agriculturally acceptable salt or ester thereof is applied at a rate of from about 0.01 to about 53 g ae/ha.

In some embodiments the florasulam is applied at a rate of about 2.3 g ai/ha to about 5.2 g ai/ha, 2,4-D or an agriculturally acceptable salt or ester thereof is applied at a rate of from about 0.26.5 to about 53 g ae/ha, and fluoroxypyr or an agriculturally acceptable salt or ester thereof is applied at a rate of from about 27 to about 53 g ae/ha.

The components of the mixtures described herein can be applied either separately or as part of a multipart herbicidal system. In some embodiments of the methods described herein, the active ingredients are applied simultaneously, including, e.g., in the form of a composition. In some embodiments, the active ingredients are applied sequentially, e.g., within 5, 10, 15, or 30 minutes of each other; 1, 2, 3, 4, 5, 10, 12, 24, 48 hour(s) of each other, or 1 week of each other.

The mixtures described herein can be applied in conjunction with one or more other herbicides to control a wider variety of undesirable vegetation. When used in conjunction with other herbicides, the composition can be formulated with the other herbicide or herbicides, tank-mixed with the other herbicide or herbicides or applied sequentially with the other herbicide or herbicides. Some of the herbicides that can be employed in conjunction with the compositions and methods described herein include, but are not limited to: 4-CPA, 4-CPB, 4-CPP, 2,4-DB, 3,4-DA, 3,4-DB, 2,4-DEB, 2,4-DEP, 3,4-DP, 2,3,6-TBA, 2,4,5-T, 2,4,5-TB, acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenteracol, fenthiaprop, fentrazamide, fenuron, ferrous sulfate, flamprop, flamprop-M, flazasulfuron, fluazifop, fluazifop-P-butyl, fluazolate, flucarbazone, flucetosulfuron, fluchloralin, flufenacet, flufenican, flufenpyrethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, flurtamone, fluthiacet, fomesafen, foramsulfuron, fosamine, fumiclorac, furyloxyfen, glufosinate, glufosinate-ammonium, glufosinate-P-ammonium, glyphosate, halosafen, halosulfuron-methyl, haloxydine, haloxyfop-methyl, haloxyfop-P-methyl, hexachloroacetone, hexaflurate, hexazinone, imazamethabenz, imazamox, imazapic, imazapyr, imazaquin, imazosulfuron, imazethapyr, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, metsulfuron-methyl, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufenethyl, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen-ethyl, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-sodium, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thifensulfuron-methyl, thiobencarb, tiocarbazil, tioclorim, topramezone, tralkoxydim, triafamone, tri-allate, triasulfuron, triaziflam, tribenuron, tribenuron-methyl, tricamba, triclopyr choline salt, triclopyr esters and salts, tridiphane, trietazine, trifloxysulfuron, trifluralin, triflusulfuron, trifop, trifopsime, trihydroxytriazine, trimeturon, tripropindan, tritac, tritosulfuron, vernolate, xylachlor and salts, esters, optically active isomers and mixtures thereof.

The compositions and methods described herein, can, further, be used in conjunction with glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, and bromoxynil on crops that are tolerant thereto, and on crops possessing multiple or stacked traits conferring tolerance to multiple chemistries and/or multiple modes-of-action.

In some embodiments, compositions provided herein further comprise at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank-mixed.

Suitable agricultural adjuvants and carriers include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$)ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8E); tallow amine ethoxylate (15 EO); PEG(400) dioleate-99.

Liquid carriers that can be employed include water and organic solvents. The organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In certain embodiments, water is the carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

In some embodiments, the compositions described herein further comprise one or more surface-active agents. In some embodiments, such surface-active agents are employed in both solid and liquid compositions, and in certain embodiments those designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; poly-ethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, and in certain embodiments, methyl esters.

In some embodiments, these materials, such as vegetable or seed oils and their esters, can be used interchangeably as an agricultural adjuvant, as a liquid carrier or as a surface active agent.

Other exemplary additives for use in the compositions provided herein include but are not limited to compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

In some embodiments, the concentration of the active ingredients in the compositions described herein is from 0.0005 to 98 percent by weight. In some embodiments, the concentration is from 0.0006 to 90 percent by weight. In compositions designed to be employed as concentrates, the active ingredients, in certain embodiments, are present in a concentration from 0.1 to 98 weight percent, and in certain embodiments, 0.5 to 90 weight percent. Such compositions are, in certain embodiments, diluted with an inert carrier, such as water, before application. The diluted compositions usually applied to weeds or the locus of weeds contain, in certain embodiments, 0.0006 to 3.0 weight percent active ingredient and in certain embodiments contain 0.01 to 0.3 weight percent.

The present compositions can be applied to weeds or their locus by the use of conventional ground or aerial dusters, sprayers, and granule applicators, by addition to irrigation or paddy water, and by other conventional means known to those skilled in the art.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Greenhouse Evaluations

Studies were applied post-emergence to broadleaf weeds reared from seed in 5" square pots in 80% mineral/20% grit field soil. Stage of growth of species at application: EPHSU in the 3 to 5 leaf stage and TRFRE in the $3^{rd}$ tri-foliate stage. Post-emergence trial design was a replicated block, one species per pot, 4 replicate pots per treatment. Post-emergence applications were made to the pot with a tracksprayer calibrated to 187 liters per hectare (L/ha), 40 pounds per square inch (PSI) at 1.9 miles per hour (mph) using an 8003E Teejet nozzle covering both soil and foliage. Trial was sub-irrigated daily. Active weed growth was maintained throughout the study period. Weed control of each species in the post-emergence study was assessed at 1, 2 and 3 weeks after treatment. Control was determined visually by comparing treated and untreated pots and scored on a 0 to 100 percent scale where 0 corresponds to no control and 100 corresponds to complete kill.

TABLE 1

Synergistic Activity of Herbicide Combinations on White Clover (TRFRE) evaluated as percent control observed 1 week after treatment

| g ai or ae/ha | | | Observed | | |
|---|---|---|---|---|---|
| Florasulam (ai) | Fluroxypyr (ae) | 2,4-D (ae) | Observed | Expected | vs. Expected |
| 0.001 | | | 10.3 | — | |
| | 0.01 | | 35 | — | |
| | | 0.11 | 1.7 | — | |
| 0.001 | 0.01 | 0.11 | 68.3 | 42.7 | 25.6 |

Field Evaluations:

Replicated applications were made to small plots (i.e. 5'×5', 3'×10') using a $CO_2$ backpack sprayer. Florasulam SC (EF-1343), fluoroxypyr (Starane® Ultra) and 2,4-D (DMA® 4) are produced by Dow AgroSciences LLC, Indianapolis, Ind. Applications at each site were made at typical postemergent herbicide timing for that particular study location. Applications were generally timed for peak dandelion bloom in the northern cool-season turf market and throughout the year in the warm-season turf market where winter and summer annual and perennial weeds are targeted. Weed control evaluations were made as percent weed cover per plot and converted to percent control based on weed levels in the untreated control. Evaluations were made at various timing after application for eight to ten weeks. Results in the following tables 2 to are presented as "Average % Weed Control".

TABLE 2

Synergistic Activity of Herbicide Combinations on Ground Ivy (GLEHE) 28 DAA from a Field Study

| g ai or ae/ha | | | Observed | | |
|---|---|---|---|---|---|
| Florasulam (ai) | Fluroxypyr (ae) | 2,4-D (ae) | Observed | Expected | vs. Expected |
| 2.3 | | | 0.0 | — | |
| | 26.5 | | 0.0 | — | |
| | | 260.6 | 41.0 | — | |
| 2.3 | 26.5 | 260.0 | 65.1 | 41.0 | 24.1 |

TABLE 3

Synergistic Activity of Herbicide Combinations on Ground Ivy (GLEHE) 56 DAA from a Field Study

| g ai or ae/ha | | | Observed | | |
|---|---|---|---|---|---|
| Florasulam (ai) | Fluroxypyr (ae) | 2,4-D (ae) | Observed | Expected | vs. Expected |
| 5.2 | | | 0.0 | — | |
| | 52.9 | | 0.0 | — | |
| | | 520 | 41.7 | — | |
| 5.2 | 52.9 | 520 | 82.7 | 41.7 | 41.0 |

TABLE 4

Synergistic Activity of Herbicide Combinations on Dandelion (TAROF) 55 DAA from a Field Study

| g ai or ae/ha | | | Observed | | |
|---|---|---|---|---|---|
| Florasulam (ai) | Fluroxypyr (ae) | 2,4-D (ae) | Observed | Expected | vs. Expected |
| 5.2 | | | 25.0 | — | |
| | 52.9 | | 14.3 | — | |
| | | 520 | 45.6 | — | |
| 5.2 | 52.9 | 520 | 77.0 | 65.0 | 12.0 |

TABLE 5

Synergistic Activity of Herbicide Combinations on White Cover (TRFRE) 62 DAA from a Field Study

| g ai or ae/ha | | | Observed | | |
|---|---|---|---|---|---|
| Florasulam (ai) | Fluroxypyr (ae) | 2,4-D (ae) | Observed | Expected | vs. Expected |
| 5.2 | | | 23.8 | — | |
| | 52.9 | | 31.3 | — | |
| | | 520 | 20.0 | — | |
| 5.2 | 52.9 | 520 | 70 | 58.1 | 11.9 |

In the foregoing examples, the following equation was used to calculate the expected activity of mixtures containing three herbicidal active ingredients:

$$\text{Expected} = 100 - \frac{(100 - A)(100 - B)(100 - C)}{10{,}000}$$

A=observed efficacy of a first active ingredient at the same concentration as used in the mixture.
B=observed efficacy of a second active ingredient B at the same concentration as used in the mixture.
C=observed efficacy of a third active ingredient C at the same concentration as used in the mixture.
The following abbreviations are used in the tables:
g ai/ha=grams active ingredient per hectare
g ae/ha=grams acid equivalent per hectare
DAA=days after application.

What is claimed is:

1. A method of controlling undesirable vegetation in turf which comprises applying to the turf where control of undesired vegetation is desired a composition comprising a synergistically effective amount of (a) florasulam (b) 2,4-D or an agriculturally acceptable salt or ester thereof, and (c) fluoroxypyr or an agriculturally acceptable salt or ester thereof; wherein the combination of (a), (b) and (c) is more effective than (a), (b) or (c) individually.

2. The method of claim 1 wherein the (a) florasulam is applied at a rate from 0.001 to about 10.3 g ai/ha, the (b) 2,4-D or agriculturally acceptable salt or ester thereof is applied at a rate from about 0.11 to about 1038 g ae/ha, and the (c) fluoroxypyr or agriculturally acceptable salt or ester thereof is applied at a rate from about 0.01 to about 105.4 g ae/ha.

3. The method of claim 1 wherein the weight ratio of (a) to (b) is from about 1:50 to about 1:200, and the weight ratio of (a) to (c) is from about 1:5 to about 1:20.

4. The method of claim 1 wherein the weight ratio of (a) to (b) is from about 1:80 to about 1:140, and the weight ratio of (a) to (c) is from about 1:7 to about 1:13.

5. The method of claim 1 wherein the (a) florasulam, (b) 2,4-D or agriculturally acceptable salt or ester thereof, and (c) fluoroxypyr or agriculturally acceptable salt or ester thereof are the only herbicidal active ingredients applied.

6. The method of claim 1 wherein the undesirable vegetation is ground ivy (GLEHE), white clover (TRFRE), dandelion (TAROF), or prostrate spurge (EPHSU).

7. The method of claim 1 wherein the weight ratio of (a) to (b) to (c) is about 1 to 110 to 10.

8. The method of claim 2 wherein the (a) florasulam is applied at a rate from about 0.001 g ai/ha to about 5.2 g ai/ha, the (b) 2,4-D or an agriculturally acceptable salt or ester thereof is applied at a rate of from about 0.11 to about 520 g ae/ha, and the (c) fluoroxypyr or an agriculturally acceptable salt or ester thereof is applied at a rate of from about 0.01 to about 53 g ae/ha.

9. The method of claim 2 wherein the (a) florasulam is applied at a rate of about 2.3 g ai/ha to about 5.2 g ai/ha, the (b) 2,4-D or an agriculturally acceptable salt or ester thereof is applied at a rate of from about 260 to about 520 g ae/ha, and the (c) fluoroxypyr or an agriculturally acceptable salt or ester thereof is applied at a rate of from about 27 to about 53 g ae/ha.

10. The method of claim 1 wherein the components of the composition are applied separately.

11. The method of claim 1 wherein the components of the composition are applied as part of a multipart herbicidal system.

12. An herbicidal composition to be applied to turf comprising a synergistically effective amount of (a) florasulam, (b) 2,4-D or an agriculturally acceptable salt or ester thereof, and (c) fluoroxypyr or an agriculturally acceptable salt or ester thereof; wherein the composition comprising (a), (b) and (c) is more effective than a composition comprising (a), (b) or (c) individually.

13. The herbicidal composition of claim 12 wherein the weight ratio of (a) to (b) is from about 1:50 to about 1:200, and the weight ratio of (a) to (c) is from about 1:5 to about 1:20.

14. The herbicidal composition of claim 13 wherein the weight ratio of (a) to (b) is from about 1:80 to about 1:140, and the weight ratio of (a) to (c) is from about 1:7 to about 1:13.

15. The herbicidal composition of claim 14 wherein the weight ratio of (a) to (b) to (c) is about 1 to 110 to 10.

\* \* \* \* \*